United States Patent [19]

Shiokawa et al.

[11] Patent Number: 5,010,093
[45] Date of Patent: Apr. 23, 1991

[54] NITRIC ESTER DERIVATIVE

[75] Inventors: Youichi Shiokawa, Ibaraki; Koichi Takimoto, Takarazuka; Kohei Takenaka, Sakai, all of Japan

[73] Assignee: Fujisawa Pharmaceutical Co., Ltd., Osaka, Japan

[21] Appl. No.: 494,545

[22] Filed: Mar. 16, 1990

Related U.S. Application Data

[62] Division of Ser. No. 213,623, Jun. 30, 1988, Pat. No. 4,923,886.

[30] Foreign Application Priority Data

Jul. 20, 1987 [GB] United Kingdom ............. 8717068

[51] Int. Cl.$^5$ ............. C07D 263/34; C07D 263/32; A61K 31/42
[52] U.S. Cl. ............. 514/374; 514/236.8; 514/326; 514/340; 514/377; 544/139; 546/209; 546/275; 548/233; 548/236
[58] Field of Search ............. 546/209, 275; 544/139; 514/236.8, 326, 340, 377, 373; 548/233, 236

[56] References Cited

U.S. PATENT DOCUMENTS 4,200,640  4/1980  Nagano et al. ............. 546/316

Primary Examiner—Robert Gerstl
Attorney, Agent, or Firm—Oblon, Spivak, McClelland, Maier & Neustadt

[57] ABSTRACT

The invention relates to a nitric ester derivative with vasodilating properties for treatment of cardiovascular disorders, the derivative being of the formula

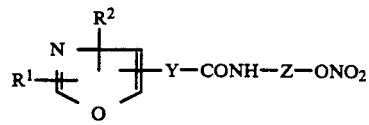

wherein
$R^1$ is hydrogen, lower alkyl, halo(lower)alkyl, halogen, phenyl, nitrophenyl, pyridyl, morpholino, piperidino, amino, lower alkanoylamino, higher alkanoylamino, benzamido, lower alkoxycarbonylamino, N-lower alkylamino, N,N-di(lower)alkylamino, N-lower alkyl-N-lower alkanoylamino, 3-lower alkylureido or N,N-di(lower) alkylamino(lower)alkyl,
$R^2$ is hydrogen, lower alkyl or N-(nitrooxy(lower)alkyl)carbamoyl,
Y is a single bond, lower alkylene or lower alkenylene, and
Z is ethylene, trimethylene, tetramethylene, 1-methylnitrooxymethylethylene, 1,1-bis(nitrooxymethyl)ethylene, 2-nitrooxytrimethylene or ethyleneoxyethylene, and pharmaceutically acceptable salts thereof.

7 Claims, No Drawings

NITRIC ESTER DERIVATIVE

This is a division of application Ser. No. 07/213,623, filed on June 30, 1988.

This invention relates to a nitric ester derivative and a salt thereof. More particularly, it relates to a new nitric ester derivative and a pharmaceutically acceptable salt thereof which have vasodilating activities, to process for the preparation thereof, and to a pharmaceutical composition comprising the same for therapeutical treatment of cardiovascular disorder in human being.

Accordingly, one object of this invention is to provide the new and useful nitric ester derivative and a pharmaceutically acceptable salt thereof, which have strong activity and much long duration of effectiveness.

Another object of this invention is to provide process for the preparation of said nitric ester derivative and the salt thereof.

A further object of this invention is to provide a useful pharmaceutical composition comprising, as an active ingredient, said nitric ester derivative or the pharmaceutically acceptable salt thereof, which is useful, as a vasodilator.

Still further object of this invention is to provide a therapeutical method for treatment of cardiovascular disorder such as coronary insufficiency, angina pectoris or myocardial infarction.

With regard to the states of the arts in this field, for example, the following compound, which is now under development, is known.

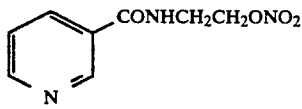

(A)

(U.S. Pat. No. 4,200,640)

However, such a known compound posseses vasodilating activities, but the duration thereof is very short. Under such situation, compounds having strong vasodilating activities and long duration are eagerly desired.

As a result of an extensive study, the inventors of the present invention could obtain the nitric ester derivative which has strong activities and long duration and is of much use as a vasodilating agent.

The nitric ester derivative of this invention can be represented by the following formula:

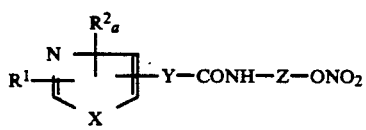

(I)

wherein $R^1$ is hydrogen, lower alkyl, halo(lower)alkyl, halogen, aryl which may have suitable substituent(s), heterocyclic group, amino which may be substituted by suitable substituent(s) or N,N-di(lower)alkylamino(lower)alkyl, $R^2$ is hydrogen, lower alkyl or N-[nitrooxy(lower)alkyl]carbamoyl, X is —O— or —S—, Y is a single bond, lower alkylene or lower alkenylene, and Z is lower alkylene which may be substituted by suitable substituent(s) or lower alkyleneoxy(lower)alkylene.

According to this invention, the object compound (I) can be prepared by the processes as illustrated by the following schemes.

Process 1

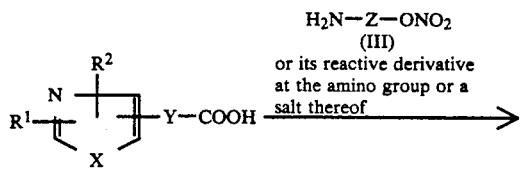

Process 2

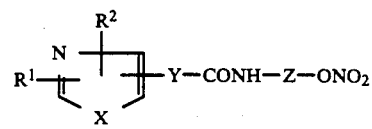

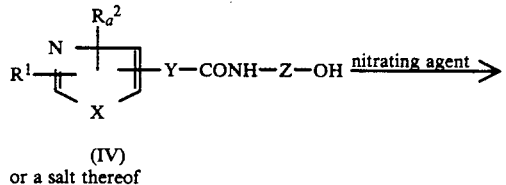

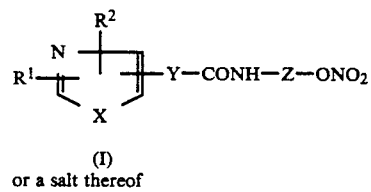

wherein $R^1$, $R^2$, X, Y and Z are each as defined above, and $R_a^2$ is hydrogen, lower alkyl or N-[hydroxy-(lower)alkyl]carbamoyl.

Among the starting compounds in the present invention, the Compound (IV) is novel and can be prepared by the processes illustrated in the following schemes or by a conventional method.

Process A

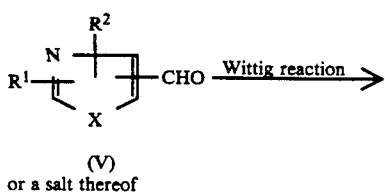

-continued

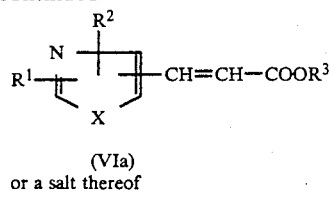

(VIa)
or a salt thereof

Process B

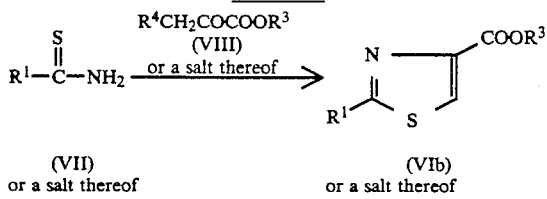

(VII)
or a salt thereof (VIb)
or a salt thereof

Process C

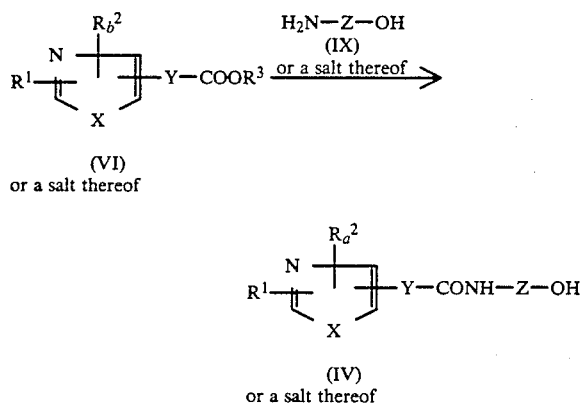

(VI)
or a salt thereof (IV)
or a salt thereof wherein $R^1$, $R^2$, $R_a^2$, X, Y and Z are each as defined above, $R_b^2$ is hydrogen, lower alkyl or —COOR$^3$ in which $R^3$ is as defined below, $R^3$ is carboxy protective group, and $R^4$ is an acid residue.

Suitable pharmaceutically acceptable salts of the object compounds (I) are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or the like.

In the above and subsequent descriptions of the present specification, suitable examples and illustrations of the various definitions which the present invention include within the scope thereof are explained in detail as follows.

The term "lower" is intended to mean 1 to 6 carbon atoms, and the term "higher" is 7 to 24 carbon atoms unless otherwise indicated.

Suitable "lower alkyl" is one having 1 to 6 carbon atom(s) and may include methyl, ethyl, propyl, isopropyl, butyl, isobutyl, tert-butyl, pentyl, tert-pentyl, hexyl, and the like, and preferably one having 1 to 4 carbon atom(s).

Suitable "halogen" may include chloro, bromo, fluoro and iodo.

Suitable "aryl" may include $C_6$–$C_{12}$ aryl such as phenyl, tolyl, xylyl, cumenyl, naphthyl, biphenylyl, and the like, which may have one or more suitable substituent(s) such as nitro, halogen as defined above, hydroxy, amino, and the like. Preferable example of such a group is phenyl and nitrophenyl (e.g. 2-nitrophenyl, 3-nitrophenyl, 4-nitrophenyl, etc.).

Suitable "heterocyclic group" may include saturated or unsaturated, monocyclic or polycyclic heterocyclic group containing at least one hetero-atom such as an oxygen, sulfur, nitrogen atom and the like. Especially preferably heterocyclic group may be 5 or 6-membered aromatic heteromonocyclic group having one to four nitrogen atom(s) (e.g. pyrrolyl, imidazolyl, pyrazolyl, triazolyl, tetrazolyl, pyridyl, pyrazinyl, pyrimidinyl, pyridazinyl, etc.), 5- or 6-membered aliphatic heteromonocyclic group having a nitrogen atom and an oxygen atom (e.g. morpholinyl, etc.), 5- or 6-membered aliphatic heteromonocyclic group having one or two nitrogen atom(s) (e.g. pyrrolidinyl, imidazolidinyl, pyrazolidinyl, piperidyl, piperazinyl, etc.), and the like, and the most preferable one is pyridyl, morpholino and piperidino.

Suitable "amino which may be substituted by suitable substituent(s)" may include amino; acylamino as mentioned below; N-lower alkylamino (e.g. N-methylamino, N-ethylamino, N-propylamino, N-isopropylamino, N-butylamino, N-isobutylamino, N-pentylamino, N-hexylamino, etc.), in which the preferred one is $C_1$-$C_4$ alkylamino, and the most preferred one is methylamino; N,N-di(lower)alkylamino (e.g. N,N-dimethylamino, N,N-diethylamino, N-ethyl-N-methylamino, N,N-dipropylamino, N,N-dipentylamino, N,N-dihexylamino, etc.), in which the preferred one is N,N-di($C_1$-$C_4$)alkylamino, and the most preferred one is N,N-dimethylamino; N-lower alkyl-N-acylamino in which the alkyl and the acyl moieties are each as defined above or below, such as N-lower alkyl-N-lower alkanoylamino (e.g. N-methyl-N-acetylamino, N-ethyl-N-acetylamino, N-propyl-N-acetylamino, N-methyl-N-propionylamino, N-hexyl-N-hexanoylamino, etc.), in which the preferred one is N-($C_1$-$C_4$)alkyl-N-($C_1$-$C_4$)alkanoylamino, and the most preferred one is N-methyl-N-acetylamino.

Suitable "N,N-di(lower)alkylamino(lower)alkyl" may include N,N-dimethylaminomethyl, N,N-diethylaminomethyl, N,N-dimethylaminoethyl, N,N-dimethylaminopropyl, N,N-dipropylaminopropyl, N,N-dihexylaminohexyl, and the like, in which the preferred one is N,N-di($C_1$-$C_4$)alkylamino($C_1$-$C_4$)alkyl, and the most preferred one is N,N-dimethylaminomethyl.

Suitable "N-[nitrooxy(lower)alkyl]carbamoyl" may include N-(nitrooxymethyl)carbamoyl, N-(2-nitrooxyethyl)carbamoyl, N-(3-nitrooxypropyl)carbamoyl, N-(4-nitrooxybutyl)carbamoyl, N-(6-nitrooxyhexyl)carbamoyl, and the like, in which the preferred one is N-[nitooxy-($C_1$-$C_4$)alkyl]carbamoyl, and the most preferred one is N-(2-nitrooxyethyl)carbamoyl.

Suitable "N-[hydroxy(lower)alkyl]carbamoyl" may include N-(hydroxymethyl)carbamoyl, N-(2-hydroxyethyl)-carbamoyl, N-(3-hydroxypropyl)carbamoyl, N-(4-hydroxybutyl)-carbamoyl, N-(6-hydroxyhexyl)carbamoyl, and the like, in which the preferred one is N-[hydroxy(C )alkyl]-carbamoyl, and the most preferred one is N-(2-hydroxyethyl)carbamoyl.

Suitable "halo(lower)alkyl" may include mono or di or trihalo(lower)alkyl such as chloromethyl, bromoethyl, difluoromethyl, trifluoromethyl, and the like, in which the preferred one is trihalo($C_1$-$C_4$)alkyl, and the most preferred one is trifluoromethyl.

Suitable "lower alkenylene" may include vinylene, propenylene, and the like, in which the preferred one is $C_2$-$C_4$ alkenylene, and the preferred one is vinylene.

Suitable "lower alkyleneoxy(lower)alkylene" may include methyleneoxymethylene, ethyleneoxyethylene, trimethyleneoxytrimethylene and the like, in which the preferred one is $C_1$-$C_4$ alkyleneoxy($C_1$-$C_4$)alkylene, and the most preferred one is ethyleneoxyethylene.

Suitable "acyl" in the term "acylamino" may include carbamoyl, N-lower alkylcarbamoyl, an aliphatic acyl group and an acyl group containing an aromatic ring (hereinafter referred to as aromatic acyl) and an acyl group containing a heterocyclic ring (hereinafter referred to as heterocyclic acyl).

Suitable example of said acyl may be illustrated as follows:

N-Lower alkylcarbamoyl (e.g. N-methylcarbamoyl, N-ethylcarbamoyl, N-propylcarbamoyl, N-isopropylcarbamoyl, N-butylcarbamoyl, N-pentylcarbamoyl, N-hexylcarbamoyl, etc.).

Aliphatic acyl such as lower or higher alkanoyl (e.g. formyl, acetyl, propionyl, butyryl, succinyl, hexanoyl, heptanoyl, lauroyl, stearoyl, etc.); lower or higher alkoxycarbonyl (e.g. methoxycarbonyl, ethoxycarbonyl, tert-butoxycarbonyl, tert-pentyloxycarbonyl, heptyloxycarbonyl, etc.); lower or higher alkanesulfonyl (e.g. methanesulfonyl, ethanesulfonyl, etc.); or the like.

Aromatic acyl such as aroyl (e.g. benzoyl, toluoyl, xyloyl, isopropylbenzoyl, naphthoyl, biphenylcarbonyl, etc.); ar(lower)alkanoyl (e.g. phenylacetyl, phenylpropionyl, etc.); aryloxycarbonyl (e.g. phenoxycarbonyl, naphthyloxycarbonyl, etc.); ar(lower)alkoxycarbonyl (e.g. benzyloxycarbonyl, phenethyloxycarbonyl, etc.); aryloxy(lower)alkanoyl (e.g. phenoxyacetyl, phenoxypropionyl, etc.); arylglyoxyloyl (e.g. phenylglyoxyloyl, naphthylglyoxyloyl, etc.); arenesulfonyl (e.g. benzenesulfonyl, p-toluenesulfonyl, etc.); or the like.

Heterocyclic acyl such as heterocycliccarbonyl (e.g. thenoyl, furoyl, nicotinoyl, etc.); heterocyclic(lower)alkanoyl (e.g. thienylacetyl, thiazolylacetyl, thiadiazolylacetyl, dithiinylacetyl, pyridylacetyl, pyrimidinylacetyl, triazolylacetyl, tetrazolylacetyl, furylacetyl, oxazolylacetyl, thiazolylpropionyl, etc.); heterocyclicglyoxyloyl (e.g. thiazolylglyoxyloyl, thienylglyoxyloyl, etc.); or the like.

Preferred example of the acyl thus defined may be:

N-lower alkylcarbamoyl, more preferably N-($C_1$-$C_4$)-alkylcarbamoyl, and the most preferably N-methylcarbamoyl; lower alkanoyl, more preferably $C_1$-$C_4$ alkanoyl, and the most preferably acetyl and butyryl; higher alkanoyl, more preferably $C_7$-$C_{15}$alkanoyl, and the most preferably lauroyl; lower alkoxycarbonyl, more preferably $C_1$-$C_4$ alkoxycarbonyl, and the most preferably methoxycarbonyl; and aroyl, more preferably $C_6$-$C_{12}$ aroyl, and the most preferably benzoyl.

Suitable "lower alkylene" is one having 1 to 6 carbon atom(s) and may include methylene, ethylene, trimethylene, propylene, tetramethylene, methyltrimethylene, dimethylethylene, hexamethylene, and the like, preferably $C_1$-$C_4$ alkylene which may have one or more, preferably one or two suitable substituent(s) such as nitrooxy.

Suitable "carboxy protective group" may include a conventional ester moiety, which may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.) or the like.

Suitable "acid residue" may include halogen (e.g. fluoro, chloro, bromo, iodo, etc.), acyloxy in which acyl moiety can be referred to as aforementioned, and the like.

The processes for preparing the object compound (I) of the present invention are explained in detail in the following.

Process 1

The object compound (I) or a salt thereof can be prepared by reacting the compound (II) or its reactive derivative at the carboxy group or a salt thereof with the compound (III) or its reactive derivative at the amino group or a salt thereof.

Suitable salt of the compounds (II) and (III) can be referred to the ones as exemplified for the compound (I).

Suitable reactive derivative at the carboxy group of the compound (II) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-1H-benzotriazole, 1-hydroxy-6-chloro-1H-benzotriazole, etc.), and the like. These reactive derivatives can optionally be selected from them according to the kind of the compound (II) to be used.

The reaction is usually carried out in a conventional solvent such as water, acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction. These conventional solvents may also be used in a mixture with water.

When the compound (II) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylim:Lne; ethoxyacetylene; 1-alkoxy-1-chloroethylene; 1,1'-(carbonyldioxy)-dibenzotriazole; 1,1'-dibenzotriazolyloxallate; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl) acetamide, mono(trimethylsilyl)acetamide, N,N-bis-(trimethylsilyl)urea, or the like; a derivative formed by reaction of the compound (III) with phosphorus trichloride or phosgene, and the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling to warming.

Process 2

The object compound (I) or a salt thereof can be prepared by reacting the compound (IV) or a salt thereof with nitrating agent.

Suitable salt of the compound (IV) can be referred to the ones as exemplified for the compound (I).

Suitable nitrating agent used in the process may include nitric acid, a combination of acetic anhydride and nitric acid or a combination of concentrated sulfuric acid and nitric acid, or the like.

The reaction temperature is not critical and the reaction is usually carried out under cooling or at ambient temperature.

The reaction is usually carried out without solvent or in a solvent such as acetic acid or other conventional solvents which do not adversely affect the reaction.

The processes for preparing the starting compound (IV) of the present invention are explained in detail in the following.

Process A

The compound (VIa) or a salt thereof can be prepared by subjecting the compound (V) or a salt thereof to Wittig reaction.

Suitable salt of the compounds (V) and (VIa) can be referred to the ones as exemplified for the compound (I).

The present reaction can be carried out by a conventional method as described in Preparation 1.

Process B

The compound (VIb) or a salt thereof can be prepared by reacting the compound (VII) or a salt thereof with the compound (VIII) or a salt thereof.

Suitable salt of the compounds (VIb), (VII) and (VIII) can be referred to the ones as exemplified for the compound (I).

The present reaction can be carried out by a conventional method as described in Preparation 5.

Process C

The compound (IV) or a salt thereof can be prepared by reacting the compound (VI) or a salt thereof with the compound (IX), or a salt thereof.

Suitable salt of the compounds (VI) and (IX) can be referred to the ones as exemplified for the compound (I).

The present reaction can be carried out by a conventional method as described in Preparation 3.

Thus obtained compound (I) may be converted into pharmaceutically acceptable salts thereof by conventional manner.

For therapeutical purpose, the nitric ester derivative (I) is administered in daily dose of 0.01 to 100 mg, preferably 0.1 to 50 mg.

The pharmaceutical compositions of this invention comprise, as an active ingredient, the nitric ester derivative (I) or pharmaceutically acceptable salt thereof in an amount of about 0.01 mg to about 50 mg, preferably about 0.01 mg to about 10 mg per dosage unit for oral and parenteral use.

One skilled in the art will recognize that the amount of the active ingredient in the dosage unit form may be determined by considering the activity of the ingredient as well as the size of the host human being. The active ingredient may usually be formulated in a solid form such as tablet, granule, powder, capsule, troche, lozenge or suppository, or a suspension or solution form such as syrup, injection, emulsion, lemonade, etc. and the like. A pharmaceutical carrier or diluent includes solid or liquid non-toxic pharmaceutically acceptable substances. Examples of solid or liquid carriers or diluents are lactose, magnesium stearate, terra alba, sucrose, corn starch, talc, stearic acid, gelatin, agar, pectin, acacia, peanut oil, olive oil or sesame oil, cacao butter, ethyleneglycol or the other conventional ones. Similarly, the carrier or diluent may include a time delay material such as glyceryl monostearate, glyceryl distearate, a wax and the like.

The object compound (I) and the pharmaceutically acceptable salt thereof of the present invention have vasodilating activities and long duration, and are useful as a vasodilating agent.

For the purpose of showing the utility of the compound (I), the pharmacological test result of the representative compound of the present invention are shown in the following.

(1) Effect on Isolated Rat Aorta Test Method

The aortas were removed from rats. Spiral strips approximately 10 mm in length were cut from the aorta, and suspended in an organ bath containing Tyrode's solution at 37° C., aerated with a gas mixture of 95% oxygen and 5% carbon dioxide. The tonus of the strips was recorded on a polygraph with a force-displacement transducer. After the initial resting tension was adjusted to 0.5 g, norepinephrine $3.2 \times 10^{-8}$ M was added to the organ bath to increase the tonus of the aortic strips to 0.9–1.1 g.

The cumulative concentrations of the test compound were then added, and finally papaverine $10^{-4}$ M was given to determine maximum relaxation. $ED_{50}$ values were calculated by interpolation from the mean cumulative dose-activity curves (effect of papaverine $10^{-4}$ M=100%).

Test Compounds

N-(2-Nitrooxyethyl)-2-methyl-4-thiazolecarboxamide hydrochloride (hereinafter referred to as Compound 1 ), and N-(2-Nitrooxyethyl)-3-pyridinecarboxamide (Reference Compound A) (hereinafter referred to as Compound A).

| Test Compounds | Test Result: ED$_{50}$ value (g/ml) |
|---|---|
| ① | $9.1 \times 10^{-8}$ |
| A | $9.4 \times 10^{-7}$ |

(2) Effect on Normotensive Rats Test Method 7 to 9-week-old male S.D. rats with mean arterial blood pressure of 100–125 mmHg, weighing 245–375 g, were used. The animals were cannulated in the left femoral artery and the mean blood pressure and heart rate were measured with a pressure-transducer. The drugs were given orally. The animals were deprived of food for about 18 hours before oral dosing. The test drugs were dissolved in saline or ethanol, and given in oral doses of 10 mg/kg. The duration of half the maximum hypotensive effect was calculated as T ½.

Test Compounds

Compound ① and Compound A.

| Test Compounds | Test Results: T ½ (minutes) |
|---|---|
| ① | 100 |
| A | 50 |

As clear from the above test results, it is evident that the compounds of the present invention have not only stronger vasodilating activities but also a much longer duration of effectiveness as compared with the reference compound, which means that the compounds of the present invention are useful for treatment of cardiovascular disorder.

The solvent used in recrystallization is given in parentheses after the melting points.

Preparation 1

Triethyl phosphonoacetate (3.04 ml) was added dropwise, with stirring, to a suspension of 62.8% sodium hydride (0.59 g) in 1,2-dimethoxyethane (26 ml) at room temperature. The solution was then stirred at the same temperature under an atmosphere of nitrogen for 30 minutes. To the solution, 2-methyl-4-thiazolecarbaldehyde (1.30 g) was added in small portions at room temperature for 10 minutes. The solvent was removed and the residue was taken up in a saturated aqueous solution (50 ml) of sodium chloride. The aqueous solution was extracted with chlorofoc.m. The chloroform extract was dried over magnesium sulfate and evaporated and the residue was subjected to column chromatography on silica gel (94 g) and eluted with chloroform. The fractions containing the objective compound were concentrated under reduced pressure to give ethyl 3-(2-methyl-4-thiazolyl)-(E)-propenate(1.56 g).

mp: 65 to 67° C.

IR (Nujol): 3105, 1700, 1626 cm$^{-1}$
NMR (CDCl$_3$, δ): 1.31 (3H, t, J=7Hz), 2.71 (3H, s), 4.26 (2H, q, J=7Hz), 6.72 (1H, d, J=15Hz), 7.40 (1H, s), 7.59 (1H, d, J=15Hz)
MASS (m/e): 197, 179, 152

Preparation 2

The following compound was obtained according to a similar manner to that of Preparation 1.
Ethyl 3-(4-thiazolyl)-(E)-propenate
mp 68° to 71° C.
IR (Nujol): 3090, 3050, 1700, 1632 cm$^{-1}$
NMR (CDCl$_3$, δ): 1.32 (3H, t, J=7Hz), 4.28 (2H, q, J=7Hz), 6.81 (1H, d, J=15Hz), 7.47 (1H, d, J=2Hz), 7.72 (1H, d, J=15Hz), 8.82 (1H, d, J=2Hz)
MASS (m/e): 183, 155, 138

Preparation 3

A mixture of ethyl 4-thiazolecarboxylate (24.49 g) and monoethanolamine (28.0 ml) was heated at 100° C. with stirring for 1 hour 20 minutes. After being cooled, the mixture was subjected to column chromatography on silica gel (245 g) and eluted with chloroform. The fractions containing the objective compound were combined and concentrated under reduced pressure to give a light brown oil of N-(2-hydroxyethyl)-4-thiazolecarboxamide (25.93 g).
IR (Nujol): 3300 (br), 1620, 1525, 1060 cm$^{-1}$
NMR (CDCl$_3$, δ): 3.58–4.15 (5H, m), 7.97 (1H, br s), 8.17 (1H, d, J=2Hz), 8.73 (1H, d, J=2Hz)
MASS (m/e): 155, 141, 112

Preparation 4

The following compounds were obtained according to a similar manner to that of Preparation 3.
(1) N-(2-Hydroxyethyl)-2-amino-4-thiazolecarboxamide
mp: 118° to 120° C. (methanol-diisopropyl ether)
IR (Nujol): 3380, 3300, 3200, 1708, 1630 (shoulder), 1616, 1062 cm$^{-1}$
NMR (DMSO-d$_6$, δ): 3.13–3.69 (3H, m), 4.76 (2H, t, J=5Hz), 7.09 (2H, br s), 7.13 (1H, s), 7.66 (1H, br t, J=5Hz)
MASS (m/e): 187, 169, 156, 127
(2) N-(2-Hydroxyethyl)-2-chloro-4-thiazolecarboxamide
IR (Nujol): 3385, 3250, 3090, 1635, 1540, 1085, 1039 cm$^{-1}$
NMR (DMSO-d$_6$, δ): 3.12–3.75 (3H, m), 4.73 (2H, t, J=5Hz), 8.23 (2H, br s)
MASS (m/e): 206, 188, 175, 146
(3) N-(2-Hydroxyethyl)-2,4-dimethyl-5-thiazolecarboxamide
mp: 81° to 83° C.
IR (Nujol): 3250 (br), 1620, 1530, 1079 cm$^{-1}$
NMR (CDCl$_3$, δ): 2.62 (3H, s), 2.65 (3H, s), 3.33–4.17 (5H, m), 6.40–6.92 (1H, m)
MASS (m/e): 200, 183, 169, 140
(4) N-(2-Hydroxyethyl)-2-methyl-5-thiazolecarboxamide
IR (Nujol): 3310, 3120, 1660, 1550, 1298, 1185, 1055 cm$^{-1}$
NMR (DMSO-d$_6$, δ): 2.67 (3H, s), 3.1–3.8 (4H, m), 4.73 (1H, t, J=5Hz), 8.21 (1H, s), 8.55 (1H, br s)
MASS (m/e): 186, 168, 155, 126, 98
(5) N-(2-Hydroxyethyl)-5-thiazolecarboxamide
IR (Nujol): 3270, 3160, 3090, 1650, 1550, 1330, 1245, 1065 cm$^{-1}$ NMR (DMSO-d$_6$, δ): 3.1–3.8 (4H, m), 4.76 (1H, t, J=5Hz), 8.52 (1H, s), 8.60 (1H, br s), 9.25 (1H, s)

MASS (m/e): 172, 154, 141, 129, 112, 84

(6) N-(2-Hydroxyethyl)-2-thiazolecarboxamide

IR (Film): 3280 (br), 1640, 1520, 1056 cm$^{-1}$

NMR (CDCl$_3$, δ): 3.08–4.17 (5H, m), 7.57 (1H, d, J=4Hz), 7.85 (1H, d, J=4Hz), 7.67–8.20 (1H, m)

MASS (m/e): 172, 154, 141, 112

(7) N-(2-Hydroxyethyl)-5-methyl-2-thiazolecarboxamide

IR (Film): 3350 (br), 1650, 1535, 1060 cm$^{-1}$

NMR (DMSO-d$_6$, δ): 2.53 (3H, s), 3.17–3.77 (4H, m), 4.75 (1H, br t, J=5Hz) 7.72 (1H, br s), 8.67 (1H, br s)

MASS (m/e): 186, 168, 155, 126

(8) N,N'-Bis(2-hydroxyethyl)-2,4-thiazoledicarboxamide mp: 155° to 158° C. (methanol-diisopropyl ether)

IR (Nujol): 3275, 1661, 1540, 1070, 1053 cm$^{-1}$

NMR (DMSO-d$_6$, δ): 3.19–3.81 (8H, m), 4.68–5.04 (2H, m), 8.47 (1H, br t, J=6Hz), 8.53 (1H, s), 8.79 (1H, br t, J=6Hz)

MASS (m/e): 259, 241, 228, 199

(9) N-(2-Hydroxyethyl)-3-(2-methyl-4-thiazolyl)-(E)-propenamide

IR (Film): 3400 (br), 1655 (br), 1540, 1093 cm$^{-1}$

NMR (DMSO-d$_6$, δ): 2.67 (3H, s), 3.11–3.60 (4H, m), 4.69 (1H, t, J=5Hz), 6.82 (1H, d, J=15Hz), 7.38 (1H, t, J=15Hz), 7.73 (1H, s), 8.20 (1H, br t, J=6Hz)

MASS (m/e): 212, 194, 182, 152

(10) N-(2-Hydroxyethyl)-3-(4-thiazolyl)-(E)-propenamide

IR (Film): 3260 (br), 3070, 1655, 1540, 1060 cm$^{-1}$

NMR (DMSO-d$_6$, δ): 2.70–3.63 (4H, m), 4.69 (1H, t, J=5Hz), 6.88 (1H, d, J=15Hz), 7.51 (1H, d, J=15Hz), 7.96 (1H, d, J=2Hz), 8.23 (1H, br t, J=6Hz), 9.19 (1H, d, J=2Hz)

MASS (m/e): 198, 180, 167, 138

(11) N,N'-Bis(2-hydroxyethyl)-2,5-thiazoledicarboxamide mp 182°–184° C. (ethanol)

IR (Nujol): 3250, 1625, 1540, 1070 cm$^{-1}$

NMR (DMSO-d$_6$, δ): 3.1–3.8 (8H, m), 4.77 (2H, t, J=5Hz), 8.51 (1H, s), 8.5–9.0 (2H, m)

MASS (m/e): 259, 241, 228, 199, 112

(12) N-(2-Hydroxyethyl)-2-methyl-4-oxazolecarboxamide mp: 62° to 63° C.

IR (Nujol): 3350, 3130, 1600, 1505, 1325, 1110, 1080 cm$^{-1}$

NMR (DMSO-d$_6$, δ): 2.46 (3H, s), 3.1–3.8 (4H, m), 4.71 (1H, t, J=5Hz), 8.0 (1H, br t, J=5Hz), 8.43 (1H, s)

MASS (m/e): 171, 152, 139, 110, 82

(13) N-(2-Hydroxyethyl)-2-trifluoromethyl-5-thiazolecarboxamide mp: 128° to 130° C. (ethyl acetate-diisopropyl ether)

IR (Nujol): 3390, 3250, 1615, 1155, 1135, 1055, 1040 cm$^{-1}$

NMR (CDCl$_3$, δ): 1.84 (1H, s), 3.5–4.1 (4H, m), 6.5 (1H, br s), 8.26 (1H, s)

MASS (m/e): 241, 222, 209, 197, 180, 152

(14) N-(2-Hydroxyethyl)-2-trifluoromethyl-4-thiazolecarboxamide mp: 100° to 101° C. (ethyl acetate-diisopropyl ether)

NMR (CDCl$_3$, δ): 2.61 (1H, m), 3.4–4.1 (4H, m), 7.8 (1H, br s), 8.43 (1H, s)

MASS (m/e): 241, 222, 209, 180, 152

(15) N-[2-(2-Hydroxyethoxy)ethyl]-2-methyl-5-thiazolecarboxamide

IR (Film) 3300, 1620, 1540, 1120 cm$^{-1}$

NMR (DMSO-d$_6$, δ): 2.67 (3H, s), 3.3–3.7 (8H, m), 4.59 (1H, t, J=5Hz), 8.24 (1H, s), 8.30 (1H, br t, J=5Hz)

MASS (m/e): 231, 200, 185, 168, 126, 98, 45

(16) N-[2-(2-Hydroxyethoxy)ethyl]-5-thiazolecarboxamide

IR (Film): 3250, 1620, 1540 cm$^{-1}$

NMR (DMSO-d$_6$, δ): 3.3–3.7 (8H, m), 4.59 (1H, t, J=5Hz), 8.52 (1H, s), 8.78 (1H, br t, J=5Hz), 9.28 (1H, s)

MASS (m/e): 217, 186, 171, 112

(17) N-(3-Hydroxypropyl)-2-xethyl-4-thiazolecarboxamide

IR (Film): 3350, 3120, 1640, 1545, 1255, 1180, 1060 cm$^{-1}$

NMR (DMSO-d$_6$, δ): 1.69 (2H, quintet J=7Hz), 2.71 (3H, s), 3.37 (2H, quartet, J=7Hz), 3.50 (2H, quarter J=7Hz), 4.52 (1H, t, J=5Hz), 8.08 (1H, s), 8.31 (1H, br t, J=7Hz)

MASS (m/e): 200, 183, 182, 170, 169, 156, 155, 126, 98, 74

(18) N-[2-(2-Hydroxyethoxy)ethyl]-2-methyl-4-thiazolecarboxamide

IR (Film): 3400, 3120, 1660, 1550, 1130, 1070 cm$^{-1}$

NMR (DMSO-d$_6$, δ): 2.73 (3H, s), 3.2–3.8 (8H, m), 4.60 (1H, m), 8.12 (1H, s), 8.21 (1H, br t, J=6Hz)

MASS (m/e): 231, 230, 212, 200, 185, 169, 168, 155, 126, 99, 98

(19) N-[2-(2-Hydroxyethoxy)ethyl]-4-thiazolecarboxamide

IR (Film): 3380 (br), 3080, 1650, 1540, 1061 cm$^{-1}$

NMR (DMSO-d$_6$, δ): 3.20–3.76 (8H, m), 4.47–4.72 (1H, m), 8.37 (1H, d, J=2Hz), 8.11–8.61 (1H, m), 9.24 (1H, d, J=2Hz)

MASS (m/e): 217, 186, 141, 112, 84

(20) N-(2-Hydroxyethyl)-2-phenyl-5-thiazolecarboxamide mp 149° to 152° C. (methanol-diisopropyl ether)

IR (Nujol): 3330, 3255, 3080, 1625, 1556, 1047 cm$^{-1}$

NMR (DMSO-d$_6$, δ): 3.17–3.74 (4H, m), 4.83 (1H, br s), 7.42–7.70 (3H, m), 7.87–8.20 (2H, m), 8.51 (1H, s), 8.78 (1H, br t, J=5Hz)

MASS (m/e): 248, 230, 217, 188, 160

(21) N-(2-Hydroxyethyl)-2-(3-nitrophenyl)-4-thiazolecarboxamide mp: 145° to 146° C. (methanol-diisopropyl ether)

IR (Nujol): 3395, 3320, 3095, 1640, 1550, 1532, 1347 cm$^{-1}$

NMR (DMSO-d$_6$, δ): 3.23–3.78 (4H, m), 4.83 (1H, t, J=5Hz), 7.86 (1H, t, J=8Hz), 8.27–8.73 (3H, m), 8.44 (1H, s), 8.86 (1H, t, J=2Hz)

MASS (m/e): 293, 275, 262, 233

(22) N-(4-Hydroxybutyl)-2-methyl-4-thiazolecarboxamide

IR (Film): 3380, 3120, 1660, 1540 cm$^{-1}$

NMR (DMSO-d$_6$, δ): 1.3–1.8 (4H, m), 2.71 (3H, s), 3.1–3.7 (4H, m), 4.39 (1H, br s), 8.07 (1H, s), 8.27 (1H, br t, J=6Hz)

MASS (m/e): 214, 196, 183, 169, 155, 126

(23) N-[2-(2-Hydroxyethoxy)ethyl]-2-methyl-4-oxazolecarboxamide

IR (Film): 3410, 3140, 1650, 1600, 1515, 1310, 1230, 1105, 1065 cm$^{-1}$

NMR (DMSO-d$_6$, δ): 2.46 (3H, s), 3.2–3.7 (8H, m), 4.4–4.7 (1H, m), 8.06 (1H, br t, J=5Hz), 8.46 (1H, s)

MASS (m/e): 184, 169, 153, 152, 139, 110, 82

(24) N-(2-Hydroxyethyl)-2-(2-nitrophenyl)-4thiazolecarboxanide mp: 84° to 86° C.

IR (Nujol): 3430, 3365, 3310, 1650, 1540 (shoulder), 1535, 1368 cm$^{-1}$

NMR (DMSO-d$_6$, δ): 3.18–3.69 (4H, m), 4.76 (1H. t, J=5Hz), 7.67–8.28 (4H, m), 8.49 (1H, s)

MASS (m/e): 293, 276, 262, 233

(25) N-(2-Hydroxyethyl)-2-methyl-4-thiazolecarboxamide mp: 68° to 70° C.

IR (Nujol): 3390, 3220, 1658, 1545, 1069 cm$^{-1}$

NMR (DMSO-d$_6$, δ): 2.73 (3H, s), 3.17–3.83 (4H, m), 4.83 (1H, br s), 8.10 (1H, s), 7.97–8.42 (1H, m)

MASS (m/e): 186, 168, 155, 126

Preparation 5

A solution of ethyl bromopyruvate (2.14 g) in ethanol (5 ml) was added to a suspension of 3-nitrobenzenecarbothioamide (2.00 g) in ethanol (15 ml) at room temperature. The reaction mixture was stirred at 50° C. for 2 hours and ten minutes. The solvent was removed by evaporation under reduced pressure. To the residue was added a saturated aqueous solution of sodium bicarbonate (50 ml) and ethyl acetate (100 ml). The precipitates were collected by filtration and recrystallized from a mixture of chloroform and n-hexane to give ethyl 2-(3-nitrophenyl)-4-thiazolecarboxylate (1.59 g).

mp: 151° to 154° C.

IR (Nujol): 3130, 3080, 1718, 1525, 1347, 1210 cm$^{-1}$

NMR (CDCl$_3$, δ): 1.45 (3H, t, J=7Hz), 4.49 (2H, q, J=7Hz), 7.68 (1H, t, J=8Hz), 8.28 (1H, s), 7.92–8.55 (2H, m), 8.83 (1H, t, J=2Hz)

MASS (m/e): 278, 250, 233, 206

Preparation 6

The following compound was obtained according to a similar manner to that of Preparation 5.

Ethyl 2-(2-Nitrophenyl)-4-thiazolecarboxylate mp: 82° to 84° C. (chloroform-n-hexane)

IR (Nujol): 3095, 1705, 1516, 1350, 1218, 1100 cm$^{-1}$

NMR (CDCl$_3$, δ): 1.42 (3H, t, J=7Hz), 4.48 (2H, q, J=7Hz), 7.53–8.17 (4H, m), 8.35 (1H, s)

MASS (m/e): 278, 248, 233, 205

Example 1

Fuming nitric acid (12.8 ml) was added dropwise to acetic anhydride (27.4 ml) with stirring and ice-sodium chloride cooling at 10° C. for 1 minute, and the mixture was stirred for 10 minutes at the same temperature. Continuously, a solution of N-(2-hydroxyethyl)-4-thiazolecarboxanide (25.0 g) in dry chloroform (35 ml) was added dropwise thereto with stirring and cooling at 5° C. for 10 minutes and the mixture was stirred for hour at the same temperature. The reaction mixture was poured into a mixture of sodium bicarbonate (100 g) and ice-water (1.0 kg) and then extracted with ethyl acetate. The extract was washed with a saturated aqueous solution of sodium chloride and dried over magnesium sulfate. The solvent was concentrated under reduced pressure and the residual solid was recrystallized from a mixture of diisopropyl ether and methanol (3:2) to give colorless crystals of N-(2-nitrooxyethyl)-4-thiazolecarboxamide (10.17 g).

mp 105° to 108° C.

IR (Nujol): 3300, 3070, 1648, 1620, 1535, 1277 cm$^{-1}$

NMR (CDCl$_3$, δ): 3.84 (2H, q, J=5Hz), 4.68 (2H, t, J=5Hz), 7.70 (1H, br s), 8.22 (1H, d, J=2Hz), 8.78 (1H, d, J=2Hz)

MASS (m/e): 171, 155, 141, 112

Example 2

The following compounds were obtained according to a similar manner to that of Example 1.

(1) N-(2-Nitrooxyethyl)-2-amino-4-thiazolecarboxamide mp: 123° to 124° C. (dec.) (n-hexane-ethylacetate).

IR (Nujol): 3350, 3280, 3175, 1635 (shoulder), 1620 (shoulder), 1605, 1542, 1522, 1282 cm$^{-1}$ NMR (DMSO-d$_6$, δ): 3.58 (2H, br q, J=5Hz), 4.63 (2H, t, J=5Hz), 7.05 (2H, br s), 7.23 (1H, s), 8.05 (1H, br t, J=5Hz)

MASS (m/e): 232, 169, 156, 127

(2) N-(2-Nitrooxyethyl)-2-chloro-4-thiazolecarboxamide mp: 58° to 60° C.

IR (Nujol): 3315, 3080, 1640 (shoulder), 1615, 1535, 1280 cm$^{-1}$

NMR (CDCl$_3$, δ): 3.81 (2H, q, J=5Hz), 4.65 (2H, t, J=5Hz), 7.47 (1H, br s), 8.03 (1H, s)

MASS (m/e): 205, 188, 175, 146

(3) N-(2-Nitrooxyethyl)-2-thiazolecarboxamide mp: 62° to 64° C.

IR (Nujol): 3280, 3085, 1650, 1520, 1275 cm$^{-1}$

NMR (CDCl$_3$, δ): 3.84 (2H, q, J=5Hz), 4.68 (2H, t, J=5Hz), 7.61 (1H, d, J=3Hz), 7.89 (1H, d, J=3Hz), 7.38–8.10 (1H, m)

MASS (m/e): 217, 171, 155, 141, 112

(4) N-(2-Nitrooxyethyl)-5-methyl-2-thiazolecarboxamide mp: 110° to 112° C. (n-hexane-ethyl acetate)

IR (Nujol): 3300, 1650 (shoulder), 1625, 1540, 1280 cm$^{-1}$

NMR (CDCl$_3$, δ): 2.55 (3H, s), 3.79 (2H, q, t, J=6Hz), 8.59 (1H, s), 8.66 (1H, br t, J=6Hz), 4.64 (2H, t, J=6Hz), 7.28–7.80 (2H, m)

MASS (m/e): 231, 185, 169, 155, 126

(5) N,N'-Bis(2-nitrooxyethyl)-2,4-thiazoledicarboxamide mp: 136° to 138° C. (ethanol)

IR (Nujol): 3410, 1671, 1625, 1610, 1540, 1281 cm$^{-1}$

NMR (DMSO-d$_6$, δ): 3.71 (4H, q, J=6Hz), 4.71 (4H, t, J=6Hz), 8.59 (1H, s), 8.66 (1H, br t, J=6Hz), 9.02 (1H, br t, J=6Hz)

MASS (m/e): 303, 286, 273, 244, 210

(6) N-(2-Nitrooxyethyl)-3-(2-methyl-4-thiazolyl)-(E)-propenamide mp: 130° to 134° C. (dec.) (ethyl acetate-diisopropyl ether)

IR (Nujol): 3200, 3105, 1645, 1610, 1550, 1280 cm$^{-1}$

NMR (CDCl$_3$, δ): 2.70 (3H, s), 3.76 (2H, q, J=5Hz), 4.63 (2H, t, J=5Hz), 6.43 (1H, br t, J=5Hz), 6.78 (1H, d, J=15Hz), 7.27 (1H, s), 7.57 (1H, d, J=15Hz)

MASS (m/e): 212, 194, 182, 152

(7) N-(2-Nitrooxyethyl)-3-(4-thiazolyl)-(E)-propenamide mp: 94° to 97° C. (dec.) (ethyl acetate-n-hexane)

IR (Nujol): 3250, 3080, 1650, 1620, 1558, 1277 cm$^{-1}$

NMR (CDCl$_3$, δ): 3.75 (2H, q, J=5Hz), 4.64 (2H, t, J=5Hz), 6.27 (1H, br s), 6.85 (1H, d, J=15Hz), 7.47 (1H, d, J=2Hz), 7.69 (1H, d, J=15Hz), 8.88 (1H, d, J=2Hz)

MASS (m/e): 243, 197, 180, 167, 138

(8) N,N'-Bis(2-nitrooxyethyl)-2,5-thiazoledicarboxamide mp: 166° C. (dec.) (ethanol)

IR (Nujol): 3300, 3230, 1625, 1610, 1515, 1275, 865, 845 cm$^{-1}$

NMR (DMSO-d$_6$, δ): 3.68 (4H, quartet, J=5Hz), 5.72 (4H, t, J=5Hz), 8.55 (1H, s), 9.13 (1H, t, J=5Hz), 9.23 (1H, t, J=5Hz)

MASS (m/e): 286, 273, 244, 210, 181

(9) N-(2-Nitrooxyethyl)-2-methyl-4-oxazolecarboxamide mp: 106° to 108° C. (ethanol)

IR (Nujol): 3380, 3090, 1650, 1630, 1605, 1510, 1280, 1010, 980, 885 cm$^{-1}$

NMR (DMSO-d$_6$, δ): 2.47 (3H, s), 3.61 (2H, quartet, J=5Hz), 4.67 (2H, t, J=5Hz), 8.49 (1H, s), 8.5 (1H, br s)

MASS (m/e): 169, 152, 139, 110, 82

(10) N-(2-Nitrooxyethyl)-2-trifluoromethyl-5-thiazolecarboxamide mp: 76° to 78° C. (diisopropyl ether)

IR (Nujol): 3320, 1625, 1550, 1290, 1280, 1150, 1040, 860 cm$^{-1}$

NMR (DMSO-d 6): 3.68 (2H, t, J=5Hz), 4.71 (2H, quartet, J=5Hz), 8.65 (1H, s), 9.30 (1H, br t, J=5Hz)

MASS (m/e): 286, 266, 239, 222, 209, 180, 152

(11) N-(2-Nitrooxyethyl)-2-trifluoromethyl-4-thiazolecarboxamide mp: 81° to 82° C. (diisopropyl ether)

IR (Nujol): 3270, 1650, 1620, 1535, 1275 cm$^{-1}$

NMR (DMSO-d$_6$, δ): 3.68 (2H, t, J=5Hz), 4.71 (2H, quartet, J=5Hz), 8.73 (1H, s), 8.86 (1H, br t, J=5Hz)

MASS (m/e): 286, 266, 239, 222, 209, 180, 152 113

(12) N-[2-(2-Nitrooxyethoxy)ethyl]-2-methyl-5-thiazolecarboxamide mp: 47° to 48° C. (ethyl acetate and diisopropyl ether)

IR (Nujol): 3310, 1610, 1560, 1275, 1120, 870, 850 cm$^{-1}$

NMR (CDCl$_3$, δ): 2.73 (3H, s), 3.4–4.0 (6H, m), 4.5–4.8 (2H, m), 6.6 (1H, br s), 8.04 (1H, s)

MASS (m/e): 276, 229, 185, 169, 155, 126, 98

(13) N-[2-(2-Nitrooxyethoxy)ethyl]-5-thiazolecarboxamide mp: 63° to 65° C. (diisopropyl ether)

IR (Nujol): 3280, 3070, 1660, 1620, 1540, 1280, 1110 cm$^{-1}$

NMR (CDCl$_3$, δ): 3.5–4.0 (6H, m), 4.5–4.8 (2H, m), 6.63 (1H, br s), 8.31 (1H, s), 8.92 (1H, s)

(14) N-2-[2-(Nitrooxyethoxy)ethyl]-2-methyl-4-oxazolecarboxamide mp: 52° to 53° C. (diisopropyl ether)

IR (Nujol): 3400, 3130, 3100, 1650, 1620, 1605, 1580, 1510, 1285, 860 cm$^{-1}$

NMR (CDCl$_3$, δ): 2.47 (3H, s), 3.5–4.0 (6H, m), 4.5–4.8 (2H, m), 7.3 (1H, br s), 8.14 (1H, s)

(15) N-(2-Nitrooxyethyl)-2-phenyl-5-thiazolecarboxamide mp: 148° to 149° C. (ethyl acetate-n-hexane)

IR (Nujol): 3300, 1622, 1550, 1278 cm$^{-1}$

NMR (CDCl$_3$, δ): 4.68 (2H, q, J=5Hz), 4.68 (2H, t, J=5Hz), 6.52–7.00 (1H, m), 7.37–7.70 (3H, m), 7.87–8.13 (2H, m), 8.23 (1H, s)

MASS (m/e): 293, 248, 230, 217, 188, 160

(16) N-(2-Nitrooxyethyl)-2-(3-nitrophenyl)-4-thiazolecarboxamide mp: 149° to 152° C. (ethyl acetate-n-hexane)

IR (Nujol): 3395, 3110, 1650, 1620, 1520, 1340, 1272 cm$^{-1}$

NMR (DMSO-d$_6$, δ): 3.71 (2H, q, J=5Hz), 4.73 (2H, t, J=5Hz), 7.83 (1H, t, J=8Hz), 8.23–8.57 (2H, m), 8.43 (1H, s), 8.83 (1H, t, J=2Hz), 8.70–9.12 (1H, m)

MASS (m/e): 338, 292, 275, 262, 233

(17) N-(2-Nitrooxyethyl)-2-(2-nitrophenyl)-4-thiazolecarboxamide

IR (Film): 3400, 3120, 1655 (shoulder), 1625, 1525, 1357, 1280 cm$^{-1}$

NMR (DMSO-d$_6$, δ): 3.64 (2H, q, J=5Hz), 4.67 (2H, t, J=5Hz), 7.70–8.30 (4H, m), 8.50 (1H, s), 8.33–8.77 (1H, m)

MASS (m/e): 338, 292, 275, 262, 235

(18) N-(2-Nitrooxyethyl)-2-methyl-4-thiazolecarboxamide mp: 78° to 79° C. (ethyl acetate—n-hexane)

IR (Nujol): 3280, 3135, 1647, 1618, 1545, 1278 cm$^{-1}$

NMR (CDCl$_3$, δ): 2.70 (3H, s), 3.64 (2H, q, J=5Hz), 4.67 (2H, t, J=5Hz), 7.72 (1H, br s), 8.00 (1H, s)

Example 3

(a) Phosphorus pentachloride (13.35 g) was added in small portions to a suspension of 2-methyl-4-thiazolecarboxylic acid (7.65 g) in dry dichloromethane over a period of 10 minutes. The resulting mixture was vigorously stirred for 1.5 hours at room temperature and then concentrated under reduced pressure. The residue was dissolved in dry benzene (40 ml) and the mixture was concentrated under reduced pressure to give yellow powders of 2-methyl-4-thiazolecarbonyl chloride (9.0 g).

(b) Triethylamine (14.91 ml) was added dropwise to a suspension of nitrate salt of 2-aminoethyl nitrate (8.18 g) in dry dichloromethane (95 ml) with ice-water cooling. 2-Methyl-4-thiazolecarbonyl chloride obtained above was added in small portions thereto at 0° to 5° C. over a period of 40 minutes. The resulting mixture was stirred for 30 minutes at the same temperature and concentrated under reduced pressure. The residue was dissolved in a mixture of water and ethyl acetate and the organic layer was separated, washed with brine and dried over anhydrous magnesium sulfate. The solvent was evaporated under reduced pressure to give an oily product of N-(2-nitrooxyethyl)-2-methyl-4-thiazolecarboxamide.

IR (Nujol): 3280, 3135, 1647, 1618, 1545, 1278 cm$^{-1}$ (c) N-(2-Nitrooxyethyl)-2-methyl-4-thiazolecarboxamide was transformed into its hydrochloride in a conventional manner, followed by recrystallization from ethanol to obtain white crystals of N-(2-nitrooxyethyl)-2-methyl-4-thiazolecarboxamide hydrochloride.

mp: 133°–134° C. (dec.)

IR (Nujol): 3200, 1660, 1620, 1285, 880 cm$^{-1}$

NMR (DMSO-d$_6$, δ): 2.71 (3H, s), 3.61 (2H, quartet, J=5Hz), 4.66 (2H, t, J=5Hz), 8.12 (1H, s), 8.60 (1H, br t, J=5Hz), 12.80 (1H, s)

MASS (m/e): 231, 185, 169, 155, 126

Example 4

(a) The following compound was obtained according to a similar manner to that of Example 3-(a).

Acetamido-4-thiazolylacetyl chloride hydrochloride

IR (Nujol): 2660 (br), 1777, 1683, 1377

(b) The following compound was obtained according to similar manners to those of Example 3-(b), and Example 3-(c) continuously.

N-(2-Nitrooxyethyl)-2-(2-acetamido-4-thiazolyl)-acetamide hydrochloride
mp: 82° to 85° C. (ethanol-diisopropyl ether)
IR (Nujol): 3420, 3240, 1699, 1650, 1612, 1540, 1380, 1279 cm$^{-1}$
NMR (DMSO-d$_6$, δ): 2.12 (3H, s), 3.27–3.68 (4H, m), 4.55 (2H, t, J=5Hz), 6.88 (1H, s), 8.00–9.33 (3H, m)
MASS (m/e): 288, 245, 225, 183, 43

Example 5

The following compounds were obtained according to similar manners to those of Example 3-(a) and Example 3-(b) continuously.

(1) N-(2-Nitooxyethyl)-2-acetamido-4-thiazolecarboxamide
IR (Nujol): 3360, 3165, 3110, 1660, 1645, 1620, 1545, 1285, 1265, 1010, 865 cm$^{-1}$
NMR (DMSO-d$_6$, δ): 2.18 (3H, s), 3.45 (1H, br s), 3.66 (2H, quartet, J=5Hz), 4.59 (2H, t, J=5Hz), 7.81 (1H, s), 8.11 (1H, t, J=5Hz)
MASS (m/e): 274, 232, 211, 198, 169, 127, 43

(2) N-(2-Nitrooxyethyl)-2-(N-methylacetamido)-4-thiazolecarboxamide
mp: 134° to 135° C. (dec.) (ethanol)
IR (Nujol): 3410, 1670, 1650, 1620, 1280, 890, 870 cm$^{-1}$
NMR (DMSO-d$_6$, δ): 2.40 (3H, s), 3.4–3.9 (2H, m), 3.75 (3H, s), 4.68 (2H, t, J=5Hz), 7.80 (1H, s), 8.51 (1H, br t, J=5Hz)
MASS (m/e): 288, 246, 212, 183, 141, 43

(3) N-(2-Nitrooxyethyl)-2-benzamido-4-thiazolecarboxamide
mp: 154° to 155° C. (dec.) (ethyl acetate diisopropyl ether)
IR (Nujol): 3355, 1650, 1630, 1535, 1285, 855, 705 cm$^{-1}$
NMR (DMSO-d$_6$, δ): 3.71 (2H, quartet, J=Hz), 4.70 (2H, t, J=5Hz), 7.4–8.4 (7H, m), 12.60 (1H, s)
MASS (m/e): 336, 283, 260, 231, 105, 77

(4) N-(2-Nitrooxyethyl)-2-(N,N-dimethylamino)-4-thiazolecarboxamide
mp: 94° to 95° C. (ethyl acetate—diisopropyl ether)
IR (Nujol): 3360, 3300, 3090, 1640, 1620, 1560, 1540, 1280, 985, 875 cm$^{-1}$
NMR (DMSO-d$_6$, δ): 3.08 (6H, s), 3.63 (2H, quartet, J=6Hz), 4.67 (2H, t, J=6Hz), 7.38 (1H, s), 8.30 (1H, br t, J=6Hz)
MASS (m/e): 260, 215, 197, 184, 155, 127

(5) N-(2-Nitrooxyethyl)-2-methylamino-4-thiazolecarboxamide
mp: 68° to 70° C.
IR (Nujol): 3350, 3220, 3110, 1645, 1630, 1585, 1540, 1285, 860 cm$^{-1}$
NMR (CDCl$_3$, δ): 3.00 (3H, s), 3.76 (2H, quartet, J=6Hz), 4.63 (2H, t, J=6Hz), 5.5 (1H, br s), 7.37 (1H, s), 7.56 (1H, br s)
MASS (m/e): 246, 183, 170, 141, 113

(6) N-(2-Nitrooxyethyl)-2,5-dimethyl-4-thiazolecarboxamide
mp: 114° to 116° C. (ethanol—diisopropyl ether)
IR (Nujol) 1650, 1610, 1280, 880 cm$^{-1}$
NMR (DMSO-d$_6$, δ): 2.64 (3H, s), 2.71 (3H, s), 3.63 (2H, quartet, J=6Hz), 4.69 (2H, t, J=6Hz), 8.49 (1H, br t, J=6Hz)
MASS (m/e): 199, 182, 169, 140

(7) N-[1,1-Bis(nitrooxymethyl)ethyl]-2-methyl-4-thiazolecarboxamide
mp: 78° to 81° C. (diisopropyl ether—n-hexane)
IR (Nujol): 3380, 3130, 1660, 1625, 1530, 1285, 995, 870, 760 cm$^{-1}$
NMR (CDCl$_3$, δ): 1.57 (3H, s), 2.70 (3H, s), 4.83 (2H, d, J=7Hz), 4.98 (2H, d, J=7Hz), 7.40 (1H, br s), 7.95 (1H, s)
MASS (m/e): 244, 126

(8) N-[1,1-Bis(nitrooxymethyl)-2-nitrooxyethyl]-2-methyl-4-thiazolecarboxamide
mp: 102° to 104° C. (ethyl acetate—diisopropyl ether)
IR (Nujol): 3250, 1650, 1630, 1270, 855 cm$^{-1}$
NMR (CDCl$_3$, δ): 2.72 (3H, s), 5.00 (6H, s), 7.60 (1H, br s), 7.98 (1H, s)
MASS (m/e): 305, 242, 126

(9) N-(2-nitrooxyethyl)-2-morpholino-4-thiazolecarboxamide
mp: 127° to 128° C.
IR (Nujol): 3200, 1632, 1603, 1516, 1282, 1230, 1108, 893 cm$^{-1}$
NMR (DMSO-d$_6$, δ): 3.2–4.0 (10H, m), 4.66 (2H, t, J=5.5Hz), 7.49 (1H, s), 8.32 (1H, br t, J=6Hz)
MASS (m/e): 302, 239, 226, 197

(10) N-(2-Nitrooxyethyl)-2-piperidino-4-thiazolecarboxamide
mp: 96° to 98° C. (dec.) (n-hexane—ethyl acetate)
IR (Nujol): 3280, 1640, 1620, 1530, 1282 cm$^{-1}$
NMR (CDCl$_3$, δ): 1.42–2.00 (6H, m), 3.22–3.93 (4H, m), 4.63 (2H, t, J=5Hz), 7.37 (1H, s), 7.47 (1H, br s)
MASS (m/e): 300, 237, 224, 195

(11) N-(2-Nitrooxyethyl)-2-phenyl-4-thiazolecarboxamide
mp: 94° to 95° C.
IR (Nujol): 3280, 1655, 1620, 1540, 1282 cm$^{-1}$
NMR (DMSO-d$_6$, δ): 3.47–3.93 (2H, m), 4.73 (2H, t, J=5Hz), 7.42–7.77 (3H, m), 7.93–8.28 (2H, m), 8.35 (1H, s), 8.60–9.03 (1H, m)
MASS (m/e): 293, 247, 230, 217, 188

(12) N-(2-Nitrooxyethyl)-2-(3-pyridyl)-4-thiazolecarboxamide
mp: 121° to 126° C. (dec.) (n-hexane—chloroform)
IR (Nujol): 3255, 1650, 1600, 1536, 1280 cm$^{-1}$
NMR (DMSO-d$_6$, δ): 3.52–3.95 (2H, m), 4.72 (2H, t, J=5Hz), 7.60 (1H, dd, J=6, 8Hz), 8.28–8.57 (2H, m), 8.63–9.05 (2H, m), 9.30 (1H, d, J=2Hz)
MASS (m/e): 294, 248, 231, 218, 189

(13) N-(2-Nitrooxyethyl)-2-lauroylamino-4-thiazolecarboxamide
mp: 122° to 126° C. (dec.) (diisopropyl ether—ethyl acetate)
IR (Nujol): 3130, 1675 (shoulder), 1630, 1542, 1281 cm$^{-1}$
NMR (CDCl$_3$, δ): 0.67–1.67 (21H, m), 2.55 (2H, br t, J=7Hz), 3.67–4.00 (2H, m), 4.65 (2H, t, J=5Hz), 7.43 (1H, br s), 7.77 (1H, s), 9.33 (1H, br s)
MASS (m/e): 414, 351, 183, 155, 127

(14) N-(2-Nitrooxyethyl)-2-butyramido-4-thiazolecarboxamide
mp: 83° to 86° C. (dec.)
IR (Nujol): 3390, 3145, 1630, 1540, 1280
NMR (CDCl$_3$, δ): 1.03 (3H, t, J=7Hz), 1.50–2.35 (2H, m), 2.53 (2H, t, J=7Hz), 3.60–4.00 (2H, m), 4.65 (2H, t, J=5Hz), 7.43 (1H, br s), 7.77 (1H, s), 9.37 (1H, br s)
MASS (m/e): 302, 239, 232, 226, 197, 169, 71, 43

(15) N-(2-Nitrooxyethyl)-2-methoxycarbonylamino-4-thiazolecarboxamide

IR (film): 3360 (shoulder), 3170, 1718, 1622 (br), 1540, 1280 cm$^{-1}$

NMR (CDCl$_3$, δ): 3.64–3.89 (2H, m), 3.91 (3H, s), 4.66 (2H, t, J=5Hz), 7.40 (1H, br s), 7.77 (1H, s), 8.29 (1H, br s)

MASS (m/e): 290, 227, 214, 185, 59

(16) N-(2-Nitrooxyethyl)-2-(3-methylureido)-4-thiazolecarboxamide mp: 128° to 132° C. (dec.) (n-hexane—ethanol)

IR (Nujol): 3360, 1700, 1620, 1530 (br), 1280 cm$^{-1}$

NMR (DMSO-d$_6$, δ): 2.73 (3H, d, J=4Hz), 3.45–3.87 (2H, m), 4.68 (2H, t, J=5Hz), 6.50–6.83 (1H, m), 7.65 (1H, s), 8.00–8.35 (1H, m), 10.48 (1H, br s)

MASS (m/e): 289, 288, 226, 212, 183, 46

(17) N-[2,3-Bis(nitrooxy)propyl]-2-methyl-4-thiazolecarboxamide

NMR (DMSO-d$_6$, δ): 2.70 (3H, s), 3.6–4.05 (2H, m), 4.4–5.2 (2H, m), 5.3–5.8 (1H, m), 7.7 (1H, br s), 7.97 (1H, s)

MASS (m/e): 306, 243, 197, 155, 126, 98

Example 6

The following compounds were obtained according to similar manners to those of Example 3-(a), Example 3-(b), and Example 3-(c) continuously.

(1) N-(2-Nitrooxyethyl)-2-butyl-4-thiazolecarboxamide hydrochloride mp: 113° to 114° C. (ethanol-diisopropyl ether)

IR (Nujol): 3180, 3050, 2580 (shoulder), 1658, 1630, 1580, 1282 cm$^{-1}$

NMR (DMSO-d$_6$, δ): 0.92 (3H, t, J=6Hz), 1.10–2.03 (4H, m), 3.03 (2H, br t, J=6Hz), 3.43–3.83 (2H, m), 4.67 (2H, t, J=5Hz), 8.13 (1H, s), 8.20 (1H, s), 8.53 (1H, br s)

MASS (m/e): 273, 227, 211, 197, 168

(2) N-(2-Nitrooxyethyl)-2-(N,N-dimethylaminomethyl)-4-thiazolecarboxamide hydrochloride mp: 119° to 120° C. (dec.) (ethanol)

IR (Nujol): 3340, 3075, 2550, 2450, 1655, 1625, 1540, 1280, 1270, 865 cm$^{-1}$

NMR (DMSO-d$_6$, δ): 2.88 (6H, s), 3.68 (2H, quartet, J=5Hz), 4.72 (2H, t, J=5Hz), 4.76 (2H, s), 8.47 (1H, s), 8.81 (1H, br t, J=5Hz), 11.5 (1H, br s)

MASS (m/e): 275, 274, 231, 185, 155, 126, 58, 44

(3) N-(2-Nitrooxyethyl)-4-methyl-5-thiazolecarboxamide hydrochloride mp: 76° to 78° C. (dec.) (ethanol-diisopropyl ether)

IR (Nujol): 3275, 3150, 2375, 1940, 1820, 1664, 1638, 1609, 1538, 1282, 1274 cm$^{-1}$ NMR (DMSO-d$_6$, δ): 2.60 (3H, s), 3.61 (2H, q, J=5Hz), 4.69 (2H, t, J=5Hz), 8.30 (2H, s), 8.67 (1H, br t, J=5Hz), 9.23 (1H, s)

MASS (m/e): 231, 185, 168, 155, 126

Example 7

The following compounds were obtained according to similar manners to those of Example 1, and Example 3-(c) continuously.

(1) N-(2-Nitrooxyethyl)-2,4-dimethyl-5-thiazolecarboxamide hydrochloride mp: 122° to 123° C. (dec.) (ethanol-diisopropyl ether)

IR (Nujol): 3175, 2270 (br), 1890, 1660, 1620, 1525, 1278 cm$^{-1}$

NMR (DMSO-d$_6$, δ): 2.57 (3H, s), 2.72 (3H, s), 3.59 (2H, q, J=5Hz), 4.67 (2H, t, J=5Hz), 8.60 (1H, br s), 12.90 (1H, br s)

MASS (m/e): 245, 199, 182, 169, 140

(2) N-(2-Nitrooxyethyl)-2-methyl-5-thiazolecarboxamide hydrochloride mp: 119° to 120° C. (dec.)

IR (Nujol): 3230, 2400, 1655, 1610, 1550, 1285, 880, 860 cm$^{-1}$

NMR (DMSO-d$_6$, δ): 2.72 (3H, s), 3.62 (2H, quartet, J=5Hz), 4.59 (2H, t, J=5Hz), 8.38 (1H, s), 9.33 (1H, br), 16.1 (1H, s)

MASS (m/e): 231, 185, 168, 155, 126, 98

(3) N-(2-Nitrooxyethyl)-5-thiazolecarboxamide hydrochloride mp: 125° C. (dec.)

IR (Nujol) 3200, 3110, 3060, 2500, 1655, 1630, 1545, 1280, 995, 860, 845 cm$^{-1}$ NMR (DMSO-d$_6$, δ): 3.64 (2H, quartet, J=5Hz), 4.71 (2H, t, J=5Hz), 8.62 (1H, s), 9.3 (1H, br s), 9.31 (1H, s), 11.80 (1H, s)

MASS (m/e): 171, 154, 141, 112, 84

(4) N-(3-Nitrooxypropyl)-2-methyl-4-thiazolecarboxamide hydrochloride mp: 133° to 135° C. (dec.) (ethanol)

IR (Nujol): 3180, 3060, 2650, 1660, 1620, 1550, 1280, 875 cm.1

NMR (DMSO-d$_6$, δ) 1.93 (2H, quintet, J=7Hz), 2.73 (3H, s), 3.38 (2H, quartet, J=7Hz), 4.58 (2H, t, J=7Hz), 8.14 (1H, s), 8.60 (1H, br t, J=7Hz), 12.03 (1H, s)

MASS (m/e): 245, 199, 183, 169, 155, 126, 98

(5) N-[2-(2-Nitrooxyethoxy)ethyl]-2-methyl-4-thiazolecarboxamide hydrochloride mp: 125–127° C. (dec.) (isopropyl alcohol)

IR (Nujol): 3190, 3060, 1650, 1630, 1560, 1290, 900, 860 cm$^{-1}$

NMR (DMSO-d$_6$, δ): 2.70 (3H, s), 3.3–3.9 (6H, m), 4.55–4.8 (2H, m), 8.13 (1H, s), 8.26 (1H, br t, J=6Hz), 9.73 (1H, s)

MASS (m/e): 276, 229, 200, 185, 169, 155, 126, 98

(6) N-(4-Nitrooxybutyl)-2-methyl-4-thiazolecarboxamide hydrochloride mp: 148° to 150° C. (dec.) (isopropyl alcohol)

IR (Nujol): 3200, 3080, 1665, 1625, 1560, 1285 cm$^{-1}$

NMR (DMSO-d$_6$, δ): 1.65 (4H, m), 2.73 (3H, s), 3.32 (2H, m), 4.57 (2H, t, J=6Hz), 8.13 (1H, s), 8.47 (1H, br), 12.57 (1H, s)

MASS (m/e): 260, 259, 213, 155, 126

(7) N-[2-(2-Nitrooxyethoxy)ethyl]-4-thiazolecarboxamide hydrochloride mp: 86° to 88° C. (ethanol-diisopropyl ether)

IR (Nujol): 3400, 3220, 3055, 1905, 1640 (br), 1540, 1280 cm$^{-1}$

NMR (DMSO-d$_6$, δ): 3.35–4.02 (6H, m), 4.58–4.90 (2H, m), 8.23 (1H, s), 8.20–8.67 (1H, m), 8.37 (1H, d, J=2Hz), 9.25 (1H, d, J=2Hz)

MASS (m/e): 215, 185, 171, 155, 141, 112

Example 8

The following compounds were obtained according to similar manners to those of Example 3-(a), and Example 3-(b) continuously.

(1) N-(2-Nitrooxyethyl)-4-thiazolecarboxamide

IR (Nujol): 3300, 3070, 1648, 1620, 1535 1277 cm$^{-1}$ (2) N-(2-Nitrooxyethyl)-2-amino-4-thiazolecarboxamide IR (Nujol): 3350, 3280, 3175, 1635 (shoulder), 1620 (shoulder), 1605, 1542, 1522, 1282 cm$^{-1}$ (3) N-(2-Nitrooxyethyl)-2-chloro-4-thiazolecarboxamide IR (Nujol): 3315, 3080, 1640 (shoulder), 1615, 1535, 1280 cm$^{-1}$ (4) N-(2-Nitrooxyethyl)-2-thiazolecarboxamide IR (Nujol): 3280, 3085, 1650, 1520, 1275 cm$^{-1}$ (5) N-(2-Nitrooxyethyl)-5-methyl-2-thiazolecarboxamide IR (Nujol): 3300, 1650 (shoulder), 1625, 1540, 1280 cm$^{-1}$ (6) N,N'-Bis(2-nitrooxyethyl)-2,4-thiazoledicarboxamide IR (Nujol): 3410, 1671, 1625, 1610, 1540, 1281 cm$^{-1}$ (7) N-(2-Nitrooxyethyl)-3-(2-methyl-4-thiazolyl)-(E)-propenamide IR (Nujol): 3200, 3105, 1645, 1610, 1550, 1280 cm$^{-1}$ (8) N-(2-Nitrooxyethyl)-3-(4-thiazolyl)-(E)-propenamide IR (Nujol): 3250, 3080, 1650, 1620, 1558, 1277 cm$^{-1}$ (9) N,N'-Bis(2.Nitrooxyethyl)-2,5-thiazoledicarboxamide IR (Nujol): 3300, 3230, 1625, 1610, 1515, 1275, 865, 845 cm$^{-1}$

(10) N-(2-Nitrooxyethyl)-2-methyl-4-oxazolecarboxamide

IR (Nujol): 3380, 3090, 1650, 1630, 1605, 1510, 1280, 1010, 980, 885 cm$^{-1}$

(11) N-(2-Nitroox/ethyl)-2-trifluoromethyl-5-thiazolecarboxamide

IR (Nujol): 3320, 1625, 1550, 1290, 1280, 1150, 1040, 860 cm$^{-1}$

(12) N-(2-Nitrooxyethyl)-2-trifluoromethyl-4-thiazolecarboxamide

IR (Nujol): 3270, 1650, 1620, 1535, 1275 cm$^{-1}$

(13) N-[2-(2-Nitrooxyethoxy)ethyl]-2-methyl-5-thiazolecarboxamide

IR (Nujol): 3310, 1610, 1560, 1275, 1120, 870, 850 cm$^{-1}$

(14) N-[2-(2-Nitrooxyethoxy)ethyl]-5-thiazolecarboxamide

IR (Nujol): 3280, 3070, 1660, 1620, 1540, 1280, 1110 cm$^{-1}$

(15) N-[2-(2-Nitrooxyethoxy)ethyl]-2-methyl-4-oxazolecarboxamide

IR (Nujol): 3400, 3130, 3100, 1650, 1620, 1605, 1580, 1510, 1285, 860 cm$^{-1}$

(16) N-(2-Nitrooxyethyl)-2-phenyl-5-thiazolecarboxamide

IR (Nujol): 3300, 1622, 1550, 1278 cm$^{-1}$

(17) N-(2-Nitrooxyethyl)-2-(3-nitrophenyl)-4-thiazolecarboxamide

IR (Nujol): 3395, 3110, 1650, 1620, 1520, 1340, 1272 cm$^{-1}$

(18) N-(2-Nitrooxyethyl)-2-(2-nitrophenyl)-4-thiazolecarboxamide

IR (Film): 3400, 3120, 1655 (shoulder), 1625, 1525, 1357, 1280 cm$^{-1}$

(19) N-(2-Nitrooxyethyl)-2-methyl-4-thiazolecarboxamide

IR (Nujol): 3280, 3135, 1647, 1618, 1545, 1278 cm$^{-1}$

Example 9

The following compounds were obtained according to similar manners to those of Example 3-(a), Example 3-(b), and Example 3-(c) continuously.

(1) N-(2-Nitrooxyethyl)-2,4-dimethyl-5-thiazolecarboxamide hydrochloride

IR (Nujol): 3175, 2270 (br), 1890, 1660, 1620, 1525, 1278 cm$^{-1}$ (2) N-(2-Nitrooxyethyl)-2-methyl-5-thiazolecarboxamide hydrochloride IR (Nujol): 3230, 2400, 1655, 1610, 1550, 1285, 880, 860 cm$^{-1}$ (3) N-(2-Nitrooxyethyl)-5-thiazolecarboxamide hydrochloride IR (Nujol): 3200, 3110, 3060, 2500, 1655, 1630, 1545, 1280, 995, 860, 845 cm$^{-1}$ (4) N-(3-Nitrooxypropyl)-2-methyl-4-thiazolecarboxamide hydrochloride IR (Nujol): 3180, 3060, 2650, 1660, 1620, 1550, 1280, 875 cm$^{-1}$ (5) N-[2-(2-Nitrooxyethoxy)ethyl]-2-methyl-4-thiazolecarboxamide hydrochloride IR (Nujol): 3190, 3060, 1650, 1630, 1560, 1290, 900, 860 cm$^{-1}$ (6) N-(4-Nitrooxybutyl)-2-methyl-4-thiazolecarboxamide hydrochloride IR (Nujol): 3200, 3080, 1665, 1625, 1560, 1285 cm$^{-1}$ (7) N-[2-(2-Nitrooxyethoxy)ethyl]-4-thiazolecarboxamide IR (Nujol): 3400, 3220, 3055, 1905, 1640 (br), 1540, 1280 cm$^{-1}$ Example 10

The following compound was obtained according to similar manners to those of Example 1, and Example 3-(c) continuously.

N-(2-Nitrooxyethyl)-2-(2-acetamido-4-thiazolyl)acetamide hydrochloride

IR (Nujol): 3420, 3240, 1699, 1650, 1612, 1540, 1380, 1279 cm$^{-1}$

Example 11

The following compounds were obtained according to a similar manner to that of Example 1.

(1) N-(2-Nitrooxyethyl)-2-acetamido-4-thiazolecarboxamide

IR (Nujol): 3360, 3165, 3110, 1660, 1645, 1620, 1545, 1285, 1265, 1010, 865 cm$^{-1}$ (2) N-(2-Nitrooxyethyl)-2-(N-methylacetamido)-4-thiazolecarboxamide IR (Nujol): 3410, 1670, 1650, 1620, 1280, 890, 870 cm$^{-1}$ (3) N-(2-Nitrooxyethyl)-2-benzamido-4-thiazolecarboxamide IR (Nujol): 3355, 1650, 1630, 1535, 1285, 855, 705 cm$^{-1}$ (4) N-(2-Nitrooxyethyl)-2-(N,N-dimethylamino)-4-thiazolecarboxamide IR (Nujol): 3360, 3300, 3090, 1640, 1620, 1560, 1540, 1280, 985, 875 cm$^{-1}$ (5) N-(2-Nitrooxyethyl)-2-methylamino-4-thiazole IR (Nujol): 3350, 3220, 3110, 1645, 1630, 1585, 1540, 1285, 860 cm$^{-1}$ (6) N-(2-Nitrooxyethyl)-2,5-dimethyl-4-thiazolecarboxamide IR (Nujol): 1650, 1610, 1280, 880 cm$^{-1}$ (7) N-[1,1-Bis(nitrooxymethyl)ethyl]-2-methyl-4-thiazolecarboxamide IR (Nujol): 3380, 3130, 1660, 1625, 1530, 1285, 995, 870, 760 cm$^{-1}$ (8) N-[1,1-Bis(nitrooxymethyl)-2-nitrooxyethyl]-2-methyl-4-thiazolecarboxamide IR (Nujol): 3250, 1650, 1630, 1270, 855 cm$^{-1}$ (9) N-(2-Nitrooxyethyl)-2-morpholino-4-thiazolecarboxamide
IR (Nujol): 3200, 1632, 1603, 1516, 1282, 1230, 1108, 893 cm$^{-1}$

(10) N-(2-Nitrooxyethyl)-2-piperidino-4-thiazolecarboxamide
IR (Nujol): 3280, 1640, 1620, 1530, 1282 cm$^{-1}$

(11) N-(2-Nitrooxyethyl)-2-phenyl-4-thiazolecarboxamide
IR (Nujol): 3280, 1655, 1620, 1540, 1282 cm$^{-1}$

(12) N-(2-Nitrooxyethyl)-2-(3-pyridyl)-4-thiazolecarboxamide
IR (Nujol): 3255, 1650, 1600, 1536, 1280 cm$^{-1}$

(13) N-(2-Nitrooxyethyl)-2-lauroylamino-4-thiazolecarboxamide
IR (Nujol): 3130, 1675 (shoulder), 1630, 1542, 1281 cm$^{-1}$

(14) N-(2-Nitrooxyethyl)-2-butyramido-4-thiazolecarboxamide
IR (Nujol): 3390, 3145, 1630, 1540, 1280 cm$^{-1}$

(15) N-(2-Nitrooxyethyl)-2-methoxycarbonylamino-4-thiazolecarboxamide
IR (film): 3360 (shoulder), 3170, 1718, 1622 (br), 1540, 1280 cm$^{-1}$

(16) N-(2-Nitrooxyethyl-2-(3-methylureido)-4-thiazolecarboxamide
IR (Nujol): 3360, 1700, 1620, 1530 (br), 1280 cm$^{-1}$

(17) N-[2,3-Bis(nitrooxy)propyl]-2-methyl-4-thiazolecarboxamide
NMR (DMSO-d$_6$, δ): 2.70 (3H, s), 3.6–4.05 (2H, m), 4.4–5.2 (2H, m), 5.3–5.8 (1H, m), 7.7 (1H, br s), 7.97 (1H, s)

Example 12

The following compounds were obtained according to similar manners to those of Example 1 and Example 3-(c) continuously.

(1) N-(2-Nitrooxyethyl)-2-butyl-4-thiazolecarboxamide hydrochloride
IR (Nujol): 3180, 3050, 2580 (shoulder), 1658, 1630, 1580, 1282 cm$^{-1}$ (2) N-(2-Nitrooxyethyl)-2-(N,N-dimethylaminomethyl)-4-thiazolecarboxamide hydrochloride
IR (Nujol): 3340, 3075, 2550, 2450, 1655, 1625, 1540, 1280, 1270, 865 cm$^{-1}$ (3) N-(2-Nitrooxyethyl)-4-methyl-5-thiazolecarboxamide hydrochloride
IR (Nujol): 3275, 3150, 2375, 1940, 1820, 1664, 1638, 1609, 1538, 1282, 1274 cm$^{-1}$

What we claim is:
1. A compound of the formula:

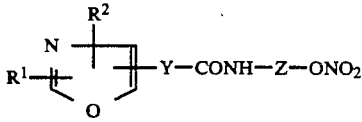

wherein
R$^1$ is hydrogen, lower alkyl, halo(lower)alkyl, halogen, phenyl, nitrophenyl, pyridyl, morpholino, piperidino, amino, lower alkanoylamino, higher alkanoylamino, benzamido, lower alkoxycarbonylamino, N-lower alkylamino, N,N-di(lower)alkylamino, N-lower alkyl-N-lower alkanoylamino, 3-lower alkylureido or N,N-di(lower) alkylamino(lower)alkyl, R$^2$ is hydrogen, lower alkyl or N-(nitroxy-(lower)alkyl) carbamoyl, Y is a single bond, lower alkylene or lower alkenylene, and Z is ethylene, trimethylene, tetramethylene, 1-methyl-nitroxymethylethylene, 1,1-bis(nitrooxymethyl)ethylene, 2-nitrooxytrimethylene or ethyleneoxyethylene, and pharmaceutically acceptable salts thereof.

2. A compound of the formula:

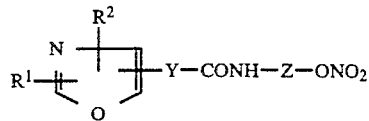

wherein
R$^1$ is hydrogen, lower alkyl, halo(lower)alkyl, halogen, aryl selected from the group consisting of phenyl, tolyl, xylyl, cumenyl, naphthyl and biphenylyl, which may have one or more substituent(s) selected from the group consisting of nitro, halogen, hydroxy and amino, pyridyl, morpholino, piperidino, amino, lower alkanoylamino, higher alkanoylamino, aroyl selected from the group consisting of benzoyl, toluoyl, xyloyl, isopropylbenzoyl, naphthoyl and biphenylcarbonyl, lower alkoxycarbonylamino, N-lower alkylamino, N,N-di(lower)alkylamino, N-lower alkyl-N-lower alkanoylamino, 3-lower alkylureido or N,N-di(lower)alkylamino(lower)-alkyl, R$^2$ is hydrogen, lower alkyl or N-(nitrooxy(lower)alkyl)carbamoyl, Y is a single bond, lower alkylene or lower alkenylene, and Z is lower alkylene selected from the group consisting of ethylene, trimethylene, propylene, tetramethylene, methyltrimethylene, dimethylethylene and hexamethylene, which may have one or two nitrooxy, or lower alkyleneoxy(lower)alkylene, in which lower alkylene is selected from the group consisting of ethylene, trimethylene, propylene, tetramethylene, methyltrimethylene, dimethylethylene and hexamethylene, and pharmaceutically acceptable salts thereof.

3. A compound of claim 1, wherein
R$^1$ is hydrogen, methyl, butyl, trifluoromethyl, chloro, phenyl, nitrophenyl, pyridyl, morpholino, piperidino, amino, acetamido, butyramido, lauroylamino, benzamido, methoxycarbonylamino, N-methylamino, N,N-dimethylamino, N-methyl-N-acetylamino, 3-methylureido or N,N-dimethylaminomethyl, R$^2$ is hydrogen, methyl or N-(nitrooxyethyl)carbamoyl, and Y is a single bond, methylene or vinylene.

4. A compound of claim 3, wherein
Y is a single bond, and
Z is ethylene.

5. A compound of claim 1, which is represented by the formula:

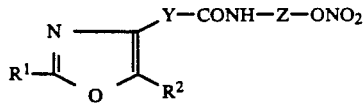

wherein $R^1$ is hydrogen or lower alkyl,
$R^2$ is hydrogen,
Y is a single bond and
Z is ethylene.

6. A vasodilating pharmaceutical composition comprising an effective amount of a compound of claim 1 or pharmaceutically acceptable salt thereof in association with a pharmaceutically acceptable, substantially non-toxic carrier or excipient.

7. A method for treating vascular disorder which comprises administering an effective amount of a compound of claim 1 or pharmaceutically acceptable salt thereof.

* * * * *